United States Patent
Freeman

(10) Patent No.: US 6,888,042 B1
(45) Date of Patent: May 3, 2005

(54) THIN FILM DRESSING WITH ABSORBENT BORDER

(75) Inventor: Frank Freeman, Abaco (BS)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/565,349

(22) Filed: May 5, 2000

Related U.S. Application Data

(63) Continuation of application No. 08/519,433, filed on Aug. 25, 1995, now Pat. No. 6,066,773, which is a continuation-in-part of application No. 08/197,047, filed on Feb. 23, 1994, now Pat. No. 5,681,579, and a continuation-in-part of application No. 08/166,623, filed on Dec. 13, 1993, now abandoned, which is a continuation of application No. 08/035,352, filed on Mar. 22, 1993, now abandoned.

(51) Int. Cl.[7] ................................................. A61F 13/00
(52) U.S. Cl. .............................. 602/52; 602/41; 602/43; 602/54; 602/56
(58) Field of Search .................. 604/336, 358, 604/367, 374, 378, 356; 602/41–59; 128/888, 889

(56) References Cited

U.S. PATENT DOCUMENTS

| | | | | |
|---|---|---|---|---|
| 3,521,631 A | * | 7/1970 | Gardner et al. | 602/57 |
| 4,373,519 A | * | 2/1983 | Errede et al. | |
| 4,538,603 A | | 9/1985 | Pawelchak et al. | |
| 4,641,643 A | * | 2/1987 | Greer | 128/888 |
| 4,738,257 A | | 4/1988 | Meyer et al. | |
| 4,909,243 A | | 3/1990 | Frank et al. | |
| 4,977,892 A | * | 12/1990 | Ewall | 602/52 |
| 5,074,852 A | * | 12/1991 | Castellana et al. | 604/336 |
| 5,092,323 A | * | 3/1992 | Riedel et al. | 602/52 |
| 5,465,735 A | | 11/1995 | Patel | |
| 5,910,125 A | * | 6/1999 | Cummings et al. | 602/58 |
| 6,066,773 A | * | 5/2000 | Freeman | 602/52 |

* cited by examiner

Primary Examiner—Kim M. Lewis
(74) Attorney, Agent, or Firm—John M. Kilcoyne

(57) ABSTRACT

A thin film device for medical applications such as a wound dressing including an occlusive layer having an edge portion about at least a portion of the thin film device and a non-continuous, hydrocolloid-containing polymeric support layer overlying the edge portion of the occlusive layer.

24 Claims, 3 Drawing Sheets

THIN FILM DRESSING WITH ABSORBENT BORDER

RELATED APPLICATIONS

This application is a continuation application of U.S. Ser. No. 08/519,433 filed Aug. 25, 1995 now U.S. Pat. No. 6,066,773 which is a continuation-in-part application of U.S. Ser. No. 08/166,623 filed Dec. 13, 1993 now abandoned and of U.S. Ser. No. 08/197,047 filed Feb. 23, 1994 now U.S. Pat. No. 5,681,579 which is a continuation application of U.S. Ser. No. 08/035,352 filed Mar. 22, 1993 now abandoned.

FIELD OF THE INVENTION

The present invention relates to thin film dressings for medical applications with a superior ability to rapidly uptake and absorb body fluid and prevent dressing leakage and wound maceration.

BACKGROUND OF THE INVENTION

Thin film dressings for medical applications are well known in the art. Thin flexible film dressings have found applications as wound dressings, incise drapes and catheter dressings. One of the first of these thin film dressings is the dressing sold under the name Opsite by Smith and Nephew. The dressings generally have a thin Polymeric film with an adhesive coating. These dressings are applied to the patient by removing a protector from the adhesive coating and adhering the dressing to the skin at the appropriate site. These thin film dressings have achieved popularity in part because the dressings are capable of readily conforming to the shape of the skin thus rendering them more comfortable for the patient to wear than has been the case in the past with other types of dressings.

One of the problems frequently encountered in the use of thin film dressings has been their sensitivity to puckering and creasing. One approach to solve the problem of puckering and creasing has been to provide a pair of non-adhesive handles at opposed edges of the adhesive dressing to facilitate the removal of the adhesive protector while the dressing is applied to the skin.

A more significant problem with thin film dressings of the prior art is encountered where these dressings are applied over wounds that produce significant quantities of exudate. Due to the occlusive nature of the thin film dressings, it is difficult to take up and absorb the exudate that has been produced by the wound in the healing process. As a result, there is a tendency for the exudate to build up under the dressing and delay and exacerbate proper wound healing.

Accordingly, it is an object of the present invention to provide a thin film dressing that provides superior exudate uptake and absorption but retains the comfort of thin film dressings.

It is another object of the present invention to provide a thin film dressing that retains the flexibility of a thin film dressing yet permits to wound to expeditiously heal where there is heavy exudation of wound fluid.

SUMMARY OF THE INVENTION

The present invention is directed to improved thin film dressings having a first layer of an occlusive material. This occlusive material is generally polymeric in nature and may include such polymeric films as polyurethanes, polyolefins and vinylidene chloride copolymers. One of the features of the occlusive layer is that the thin film dressing is relatively impervious to moisture i.e., has a moisture vapor rate transmission in the range of about 450 to 3000 MVTR (moisture vapor transmission rate) as measured by ASTM test E96 at 100° F. and 90° relative humidity.

Securely attached to the occlusive layer is a second layer which provides for the rapid uptake of wound exudate and/or other body fluids. As used hereinafter the term "body fluid" shall include all fluids which are produced by and/or emanate from the body including, but not limited to wound exudate. The second layer may optionally include an absorbent region which contains one or more materials capable of absorbing body fluids.

In accordance with the present invention, the second layer is a non-continuous polymeric support which may be in the form of a web, net, perforated layer or perforated film or the like. The second layer is made of a suitable polymeric material and contains or has associated therewith one or more hydrocolloids to promote wound healing and one or more optional absorbents.

Of particular importance to the present invention is that the second layer with or without the absorbent region does not cover the entire surface of the occlusive layer. Preferably the second layer is placed about the perimeter portion of the occlusive layer leaving a portion of the occlusive layer usually at or about its center free of the second layer. In this embodiment, the portion of the occlusive layer free of the second layer is situated over the wound surface. The second layer provides for the rapid uptake of the body fluid and prevents a buildup of such fluid from delaying proper healing of the wound.

More specifically, the present invention is directed to a thin film device comprising:

a) an occlusive layer having an edge portion about at least a portion of the perimeter of the film and a body portion; and b) a non-continuous, hydrocolloid-containing polymeric support layer overlying the edge portion of the occlusive layer.

The polymeric support layer preferably contains an absorbent region preferably containing one or more absorbents. In another preferred form of the invention, the occlusive layer and the polymeric support layer are bonded together to provide a thin sealed edge at the edge portion of the occlusive layer.

BRIEF DESCRIPTION OF THE DRAWINGS

The following drawings in which like reference characters indicate like parts are illustrative of embodiments of the invention and are not intended to limit the invention as encompassed by the claims forming part of the application.

DETAILED DESCRIPTION OF THE INVENTION

Figure 1:
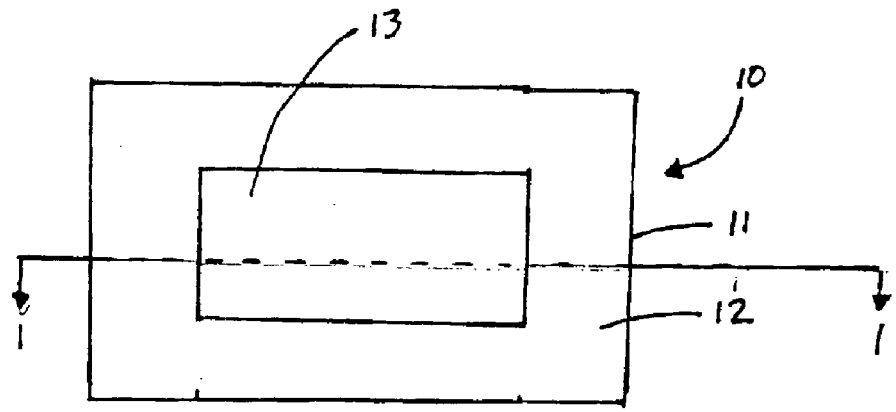
FIG. 1 is a bottom view of an embodiment of a wound dressing of the present invention.

As shown in FIG. 1 the dressing 10 of the present invention is provided with a thin film or occlusive layer of a polymeric material 11. The polymeric material may be any thickness desired. The preferred thickness is in the range of from about 0.5 to 10 mils. More preferably, the thin films of the present invention are from about 1 to 3 mils thick. The selection of the particular polymeric material is principally based on the moisture vapor transmission rate (MVTR) of the polymeric material rather than its thickness. Thus, the thin polymeric films are preferably selected based on their relative imperviousness to moisture and typically have a MVTR of from about 450 to 3000 as measured by ASTM. There are a number of materials suitable for thin films employed in the present invention that will have a MVTR in the desired range. Such materials include polymeric films or foams such as polyurethanes, polyolefins (e.g. polypropylenes, polyethylene and copolymers thereof) and vinylidene chloride copolymers.

Suitable polyethylenes include low density polyethylene, linear low density polyethylene and ultra low density polyethylene. Ultra linear low density polyethylenes are generally polyethylene having a density of below 0.910 gm α-1. Another suitable polyolefin is ethylene vinyl acetate (EVA). Preferably the EVA has a vinyl acetate content below about 25%. More preferably an EVA with a vinyl acetate content of about 18% may be used as the occlusive layer.

Other polymeric materials that may be used as the thin film layer are vinylidene chloride and copolymers, such as copolymers of vinylidene chloride and vinyl chloride or alkyl acrylates such as methyl acrylate and methyl methacrylate. Such vinylidene chloride copolymers are generally sold under the trademark Saran.

The preferred polymeric materials for the thin film are polyurethanes, polypropylenes and ethylene vinyl acetates. The polyurethanes may be either an ester or ether based polyurethane having a 6800 PSI and an elongation of from about 300 to 750. The thin film dressings may also be constructed of elastomeric polyurethane or polyester polymers. The copolyester ether elastomers sold under the trademark Hytrel by Dupont may also be used.

The thin film layer 11 may if desired have a hydrocolloid material present. The hydrocolloid may be applied to the surface of the thin film such as by means of an adhesive or by means of heat or ultrasonic bonding. Another method of applying a hydrocolloid material to the thin film layer 11 is to brush on a solution containing a hydrocolloid. Alternatively, the hydrocolloid may be blended in with the polymeric resin prior to extrusion to form the film. One approach to blending the hydrocolloid in the thin film is to use a twin screw extruder to extrude granulated polymer such as EVA. The extrudate is thin re-extruded and the hydrocolloid material is mixed into the polymer in a section of the screw. The polymeric material containing the hydrocolloid is then extruded to form a film. The polymeric material may also be cast or blown by conventional techniques.

An alternate method of applying the hydrocolloid material to the thin film is by applying a solution of the hydrocolloid to the film having a concentration of from about 2 to 3%. The hydrocolloid is preferably in an aqueous solution although other suitable solvent vehicles may be used. In another embodiment, a solution such as a 10% suspension of a hydrocolloid in a gelled mineral oil, petroleum jelly, a suppository base such as Huls Witespol Softisan or other suitable carrier may be used. The suppository base is generally a vegetable fatty acid having a $C_{10}$–$C_{18}$ length carbon chain. Suitable hydrocolloids for use in the thin film layer 11 include any water soluble gum such as pectin, gelatin, carboxymethyl cellulose (CMC) such as sodium CMC, sodium or calcium alginate fibers, polysaccharides and the like. The hydrocolloid may also contain additional materials such as antibiotics or growth factors and silver sulfadiazine or other antibacterial products. The hydrocolloid may be present in the film layer 11 either with or without accelerators to promote release thereof which are known in the art. A typical accelerant is a surfactant.

Figure 2:
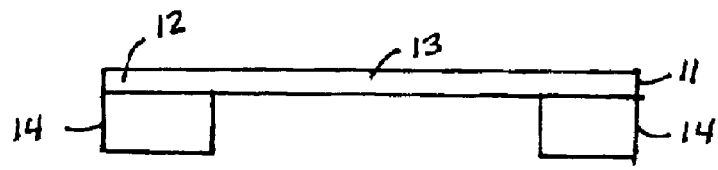
FIG. 2 is a cross-sectional view of the dressing shown in FIG. 1 taken along line 1—1.

The occlusive layer has an edge portion 12 and a body portion 13. About the edge portion 12 of the dressing is a non-continuous polymeric support layer 14 as shown in FIG. 2. The purpose of the polymeric support layer 14 is to provide for the rapid uptake of body fluids (e.g. fluid exuded by the wound) during the healing process. If the body fluid is not rapidly removed by the dressing there is a tendency for the body fluid to pool on the surface of the wound or the surrounding skin under the dressing. As a result, the healing process is inhibited and healthy skin adjacent the wound may be damaged because of contact with moisture.

The polymeric support layer 14 is adhered to the occlusive layer 11 by any suitable bonding means. One such bonding means is the use of adhesive provided on the surface of the occlusive layer 11. The adhesive may, for example, extend across the entire under surface of the occlusive layer 11 or only a portion of it. An alternate bonding means is, for example, heat or ultrasonic bonding.

The polymeric support layer 14 can be of any polymeric material useful in medical settings and typically is in the form of a web, net, perforated film, perforated layer or the like. Suitable materials include polyolefins such as polyethylenes (with and without acetate moieties, e.g., ethylene vinyl acetate), polypropylenes, polyesters and the like. Other suitable polymeric materials include water soluble polymers such as polyvinylpyrrolidones, polyvinyl-alcohols and the like. One such preferred polymeric material is ethylene vinyl acetate (EVA), available, for example, as Union Carbide's Natural 7 or EVATANE 1020 VN5 or 1080 VN5. The EVA preferably has a vinyl acetate content of about 15 to 28% and more preferably about 18%. The polymeric material, such as EVA, preferably has a melting temperature of about 105° C. or below since at temperatures above 105° some degradation of hydrocolloids is possible. Another suitable polymeric material is Delnet, a product of Applied Extrusion Technologies which includes a range of materials manufactured from polyethylene or polypropylene using extrusion embossing and orientation processes.

The polymeric support layer 14 contains a hydrocolloid either blended with the polymeric material or coated thereon. When the hydrocolloid is blended with the polymeric material it is preferred that the two materials be extruded together to form a film. The polymeric support layer 14, when it is a blend of hydrocolloid and a polymeric material, can be formed by any suitable process. One process that has been found to be suitable is the use of a twin screw extruder to extrude the polymeric material such as EVA and the hydro collid material which is mixed into the EVA in a section of the screw. The EVA containing hydrocolloid material is then extruded to form a film which can be laminated or adhered to the occlusive layer 11 by any conventional process. The hydrocolloid material can also be formed by conventional casting or blowing techniques.

Prior to adhering the so formed hydrocolloid containing polymeric support layer 14 to the occlusive layer 11 a fluid path is provided in the polymeric support layer 14 to enable the rapid uptake of the body fluid. The fluid path is generally provided by perforations, the size and shape of which may vary over a wide range so long as the perforations provide a pathway for the rapid uptake of body fluid.

The perforations may be formed by any suitable means. One such means of perforating the polymeric support layer 14 is by passing the film over a heated roll or, alternatively the holes are punched into the film mechanically. Another method of perforating the polymeric support layer 14 is by extruding the layer, embossing it on a roll and biaxially orienting the layer. It is preferred that there be at least 40 perforations to a square inch in the polymeric support layer 14.

In an alternate embodiment of the invention, the polymeric support layer 14 can be a thin perforated polyethylene or polypropylene film such as that sold under the trademark Delnet. This thin perforated film can be coated with the hydrocolloid material by a suitable means. In one method of applying the hydrocolloid material, the hydrocolloid can be applied by coating a thin perforated film with about a 2 or 3% solution of the hydrocolloid in water. When an aqueous solution of hydrocolloid is being applied to the thin perforated film, the thin film may be treated by corona discharge methods to promote adhesion of the hydrocolloid. In an alternative embodiment, a solution such as a 10% suspension of hydrocolloid in a gelled mineral oil, petroleum jelly, a suppository base such as Huls Witespol Softisan, or other suitable carrier may be used. The suppository base is generally a vegetable fatty acid having a $C_{10}$–$C_{18}$ length carbon chain.

The hydrocolloid materials useful for the polymeric include the same hydrocolloids which may optionally be included in the occlusive layer 11. Such hydrocolloid materials include any water soluble gum (e.g. pectin, guar gum, xantham gum), gelatin, carboxymethylcellulose (CMC), such as sodium CMC, sodium or calcium alginates, polysaccharides and the like. The hydrocolloid material may also include additional materials such as antibiotics or growth factors and silver sulfadiazine or other antibacterial products. The hydrocolloid may be present in the polymeric support layer 14 either with or without accelerators to promote release, such as surfactants, known in the art.

Figure 3:
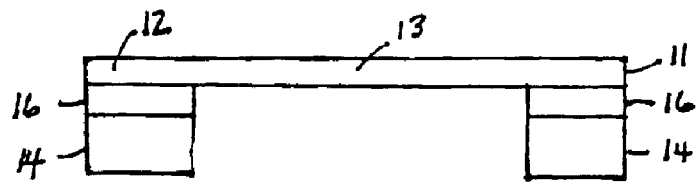
FIG. 3 is a cross-sectional view of the dressing similar to the embodiment shown in FIG. 2 containing an absorbent region.

Depending on the type of wound and the amount of body fluid additional layers may also be present in the dressing of the present invention. Between the occlusive layer 11 and the polymeric support layer 14 may be an adsorbent region 16 as shown in FIG. 3. Additional hydrocolloid material and/or superabsorbents are preferably present in the absorbent region 16 to promote absorption and wound healing.

The material of the absorbent region 16 can be a fabric, foam, fiber or the like, including combinations thereof, which is capable of both absorbing fluids and bonding to the occlusive layer 11 and the polymeric support layer 14. The absorbent region 16 can be made up of the known pulp products either with or without hydrocolloid or superabsorbent material. The degree of absorbency desired depends on the use of the thin film device (e.g. the type of wound being treated).

The absorbent region 16 can be any of the materials used in wound care which can absorb body fluid. Materials that may be used in the absorbent region include fabrics, foams, fibers or structures of polyester, polypropylenes, polyethylenes and the like which are optionally bonded to polyester film (such as Novenette distributed by Kendall). Other suitable materials which may be included in the absorbent region 16 include, but are not limited to, natural and synthetic polymeric absorbents, hydrocolloids, superabsorbents, and cellulosic absorbents.

Cellulosic materials include cotton, rayon, wood, or cellulose. The superabsorbent material may be in any suitable form. Typical superabsorbents include starch grafted copolymers of acrylate salts, starch grafted copolymers of acrylamide salts, polyacrylate salts and the like, including mixtures thereof. Superabsorbent materials and composites are easily prepared or commercially available. The superabsorbent can also be formed by needle punction processes. One such product is the composite air laid superabsorbent pad (dry forming process and the superabsorbent fiber flock SAFF) sold by Hanfspinnern Steen & Company. The superabsorbent may also be a delayed release web superabsorbent.

Superabsorbent webs that may be used in the present invention to serve as, or to be incorporated into, the absorbent region 16 may also include carded or random webs made from, for example, cotton, rayon, polyethylene, polyester, or wool. Another suitable web is a spun-laced web made from polyester, polypropylene, or polyethylene. The superabsorbent webs may also be in the form of tissues either single ply or multiple ply and either creped or uncreped. Delnet, a product of Applied Extrusion Technologies as previous described among the polymeric support materials may also be used as a web for preparing a superabsorbent web.

Superabsorbent webs can be formed by any convenient means, e.g., by slightly moistening or misting a web. After misting, a powdered superabsorbent may be applied followed by passing the web through a dry oven or heating the roll. The powder adjacent to the moistened web will become tacky and adhere to the adjacent material (fiber, surface), and the loose powder is then be vacuumed off. Alternatively, superabsorbent powder can be sandwiched between nonwoven webs/paper and subjected to moist steam which would make the superabsorbent tacky so that it would then stick to adjacent surfaces. The sandwiched superabsorbent and web would then be dried, creating a two-ply web with superabsorbent between them. The superabsorbent layer can also be heat bonded to the other layers.

Figure 4:
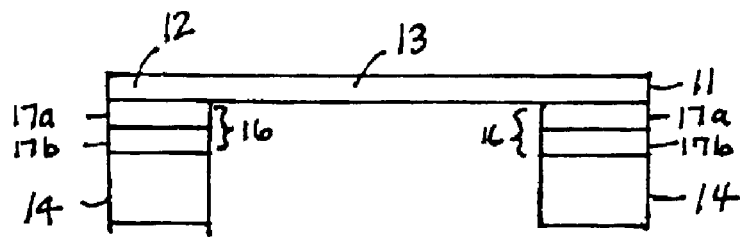
FIG. 4 is a cross-sectional view of another embodiment of the dressing of the present invention.

As shown in FIG. 4 the absorbent region 16 may be a multilayer laminate having at least two layers 17 (two layers 17a and 17b are specifically shown in FIG. 4). The layers may be each composed of the same absorbent materials mentioned above for use in the absorbent region 16 including fabrics, foams or fibers of polyester, polypropylenes, polyethylenes which optionally bonded to polyester film (such as Novenette distributed by Kendall).

The polymeric layer 14 may be bonded to the occlusive film 11 with suitable adhesives such as acrylic or suitable hot melts. Instead of an adhesive the polymeric layer may be bonded to the film by heat or ultrasonic bonding.

Figure 5:
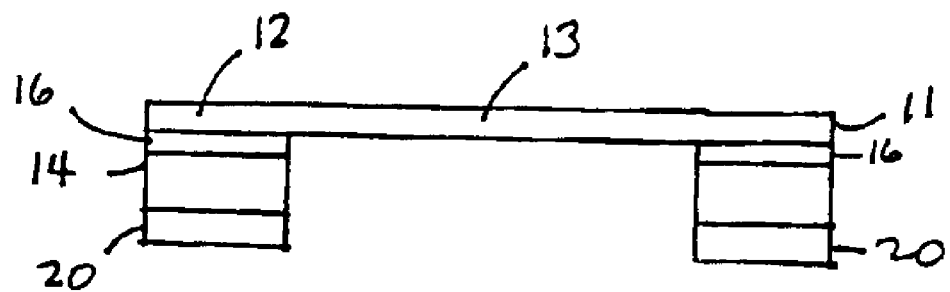
FIG. 5 is a cross-sectional view of a further embodiment of the dressing of the present invention.

In addition to the polymeric support layer 14 the occlusive layer 11 and the absorbent region 16, additional layers may be present if desired. For example, the polymeric support layer 14 may have a wound contact layer 20 as shown in FIG. 5 in contact with the skin. The wound contact layer 20 may be made of a non-adhering wound dressing material on its surface. Preferred non-adhering wound dressing materials are polyolefins such as a polyethylene or a polypropylene. The polyethylene can include an ethylene vinyl acetate. The non-adhering layer is preferably formed by using an extrusion embossing or an orientation process. An example of the non-adhering wound dressing material is Delnet sold by Applied Extrusion Technologies. An alternative material is a high, wet strength, non-woven, low-cling material impregnated with HCD's carried in a solution of, for example, polyvinylpyrrolidone (PVP) in isopropyl alcohol.

An adhesive may if desired be placed on the layer of the dressing that contacts the skin (e.g. the polymeric support layer 14 or the wound contact layer 20). The adhesive composition may be any suitable adhesive such as one based on a high molecular weight polyisobutylene or an acrylic based adhesive. The adhesive may include an homogeneous blend of one or more pressure sensitive adhesive materials and one or more natural or synthetic polymers capable of developing elastomeric properties when hydrated such as gluten and long chain polymers of methyl vinyl ether/maleic acid. The composition may also include one or more water-soluble hydrocolloid gums and may additionally include one or more water swellable cohesive strengthening agents. Additionally, one or more thermoplastic elastomers may be included with the pressure sensitive adhesive materials.

Various natural or synthetic viscous or elastomeric substances as natural rubber, silicone rubber, acrylonitrile rubber, polyurethane rubber, polyisobutylene, etc., either possessing dry tack by themselves or developing such tack upon the addition of a plasticizer are suitable as adhesives. Low molecular weight polyisobutylenes having a viscosity average molecular weight of from about 36,000 to about 58,000 (Florey) may also be used.

Optionally, one or more thermoplastic elastomers can be included in the pressure sensitive adhesive component. These elastomers impart the properties of rubber-like extensibility and both rapid and complete recovery from modular strains to the pressure sensitive adhesive component. Suitable thermoplastic elastomers include medium molecular weight polyisobutylenes having a viscosity average molecular weight of from about 1,150,000 to 1,600,000 (Florey), butyl rubber which is a copolymer of isobutylene with a minor amount of isoprene having a viscosity average molecular weight of from about 300,000 to about 450,000 (Flory), and styrene copolymers such as styrene-butadiene-styrene (S-B-S) styrene-isoprene-styrene (S-I-S), and styrene-ethylene (S-EB-S) which are commercially available, for example, from Shell Chemical Co. under the trademark Kraton as Kraton D1100, D1102, Kraton D1107, Kraton 4000, Kraton G1600, and Kraton G4600. Thermoplastic elastomers such as butyl rubber having a viscosity average molecular weight of about 425,000 (commercially available as gauge 077), polyisobutylene having a viscosity average molecular weight of about 1,200,000 (commercially available under the trademark Vistanex from Exxon as gauge L-100), and styrene-isoprene-styrene (S-I-S) copolymers (commercially available from Shell as Kraton D1107). In this case of polyisobutylene (PIB) based adhesives, a perforated film can be used to support a thin layer of these materials. The perforations permit fluid flow when the PIB disintegrates.

The natural or synthetic polymers which develop elastomeric properties when hydrated may be present at from about 3% to about 60% by weight of the adhesive composition. The preferred materials are the long chain polymers of methyl vinyl ether/maleic acid. The maleic acid moiety in the polymer may be intact (Gantrez S-97), may be an anhydride (Gantrez AN-169), or may be a metal salt such as the mixed sodium/calcium salts (Gantrez AT-955). These materials are hydrophilic and when hydrated form extensible elastic masses with substantial tack to skin and other surfaces. The adhesive composition may also include up to about 30% by weight of one or more water swellable cohesive strengthening agents provided that the water soluble hydrocolloid gums and water swellable cohesive strengthening agents provided that the water-soluble hydrocolloid gums and water swellable cohesive strengthening agents provided that the water-soluble hydrocolloid gums and water swellable cohesive strengthening agents together are present at no more than about 60% by weight of said adhesive composition. Suitable water swellable cohesive strengthening agents include finely divided substantially water insoluble cross-linked sodium carboxymethylcellulose such as that commercially available under the trademark Aqualon, finely divided substantially water-insoluble starch-acrylonitrile graft copolymer, finely divided substantially water-insoluble cross-linked dextran.

The adhesive composition may also include up to about 50% by weight of one or more water-soluble hydrocolloid gums. Between the non-adhering wound dressing layer and the absorbent layer is water-soluble film layer such as a film of polyvinylpyrrolidone film sold by BASF and GAF. This film preferably contains a hydrocolloid gum. Suitable hydrocolloid gums may include sodium carboxymethylcellulose, pectin, gelatin, guar gum, locust bean gum, and gum karaya. The film may also be gelled mineral oil or petroleum jelly containing hydrocolloids.

The adhesive coating can suitably have a thickness of 0.5 mil to 1.5 mil.

The adhesive coating can be continuous or a discontinuous coating, for example, a pattern, porous or microporous coating.

Figure 6:
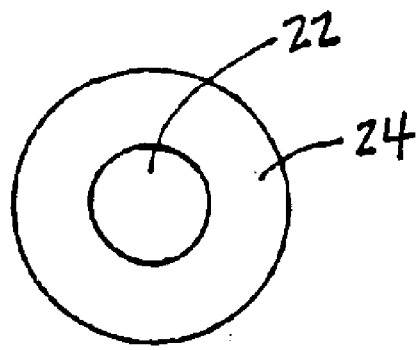
FIG. 6 is a bottom view of a still further embodiment of the dressing of the present invention.

As seen in FIG. 6 the dressing of the present invention may take a variety of shapes as desired for particular wound applications. In FIG. 6 the body portion 22 is free of the polymeric support layer while the edge portion 24 is provided with the polymeric support layer and optionally the absorbent region.

Figure 7:
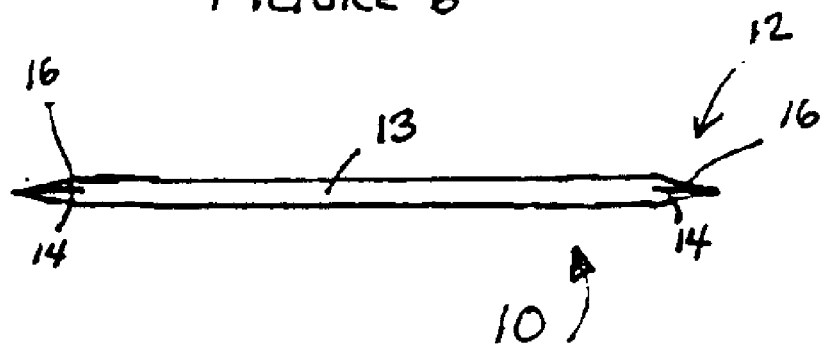
FIG. 7 is a cross-sectional view of a dressing similar to the embodiment shown in FIG. 2 wherein the occlusive layer and the polymeric support layer are compressed and then sealed to provide a tapered edge portion.

An alternate and preferred embodiment of the present invention is shown with reference to FIG. 7. The occlusive top layer and the adjacent lower layer can be compressed and then sealed to form a tapered edge.

More specifically, the dressing 10 has an edge portion 12 which is compressed into a thin edge portion having a thickness of preferably from about 2 to 5 mils. The embodiment represented by FIG. 7 is prepared by taking the embodiment of FIG. 3 and compressing the edge portion 12 and then sealing the edge portion. Compression can be performed by using a horn coming down into a shaped anvil. The compressed edge portion is then sealed, preferably by ultrasonic bonding.

Figure 8:
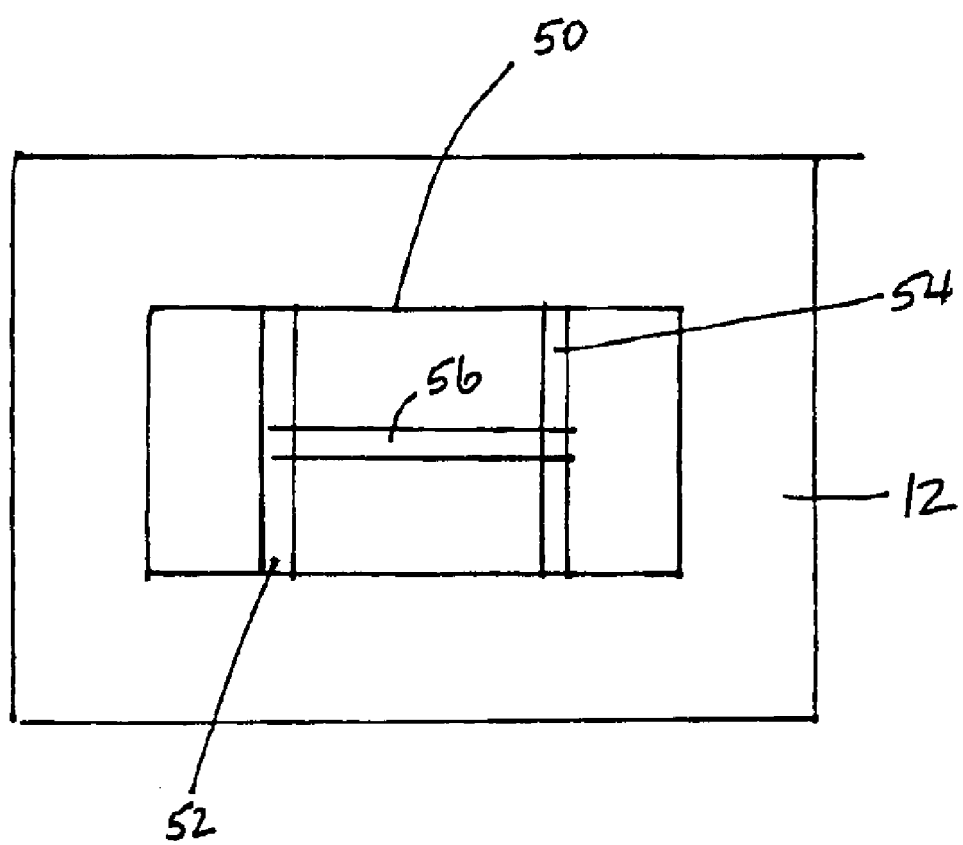
FIG. 8 is a bottom view of still another embodiment of the dressing of the present invention.

In another embodiment of the invention as shown in FIG. 8 the body portion 50 of the thin film layer 11 may be bridged by one or more thin strands of absorbent material 52, 54 and 56 which provide additional absorption of wound exudate. These bridged portions may be of the same absorbent material as the absorbent border or may be of a different type of absorbing material. This thin strand may be as shown or in any suitable configuration as desired. The thin strand is preferably adhered to the occlusive layer by a suitable adhesive means.

What is claimed is:
1. A thin film device for medical applications comprising:
   a) an occlusive layer having a perimeter and an edge portion about at least a portion of the perimeter of the occlusive layer and a body portion, said body portion being spaced apart from the user;

b) a non-continuous, hydrocolloid-containing polymeric support layer in the form of a web, net or perforated film, said polymeric support layer being made of a material and constructed so as to permit rapid uptake of body fluids emanating from a wound, overlying the edge portion of the occlusive layer; and c) a non-adhering layer attached to the polymeric support layer, said non-adhering layer having an adhesive thereon for attaching to the skin of the user.

2. The thin film device of claim 1 wherein the edge portion extends about the entire perimeter of the thin film dressing.

3. The thin film device of claim 1 wherein the occlusive layer is impervious to moisture.

4. The thin film device of claim 1 wherein the occlusive layer has a moisture vapor transmission rate of from about 450 to 3000 MVTR.

5. The thin film device of claim 1 wherein the occlusive layer is made from a material selected from the group consisting of polyolefins, polyurethanes, and vinylidene chloride copolymers.

6. The thin film device of claim 1 wherein the occlusive layer further comprises a hydrocolloid.

7. The thin film device of claim 1 wherein the polymeric support layer contains more than one hydrocolloid.

8. The thin film device of claim 1 wherein the hydrocolloid is incorporated into the polymeric support layer.

9. The thin film device of claim 1 wherein the hydrocolloid is coated onto the polymeric support layer.

10. The thin film device of claim 1 wherein the polymeric support layer has a surface having an adhesive thereon for attaching to the skin of the user.

11. The thin film device of claim 1 wherein said polymeric support layer is adhered to said occlusive layer by an adhesive.

12. The thin film device of claim 1 wherein said polymeric support layer is adhered to said occlusive layer by heat.

13. The thin film device of claim 1 wherein said polymeric support layer is adhered to said occlusive layer by ultrasonic bonding.

14. The thin film device of claim 1 further comprising an absorbent material attached to the body portion of the occlusive layer.

15. The thin film device of claim 14 wherein the absorbent material attached to the body portion of the occlusive layer is in the form of intersecting strands.

16. The thin film device of claim 1 wherein the occlusive layer and the polymeric layer are compressed and sealed together at the edge portion thereof.

17. The thin film device of claim 1 in the form of a wound dressing.

18. The thin device of claim 17 wherein the wound dressing comprises:

a) said occlusive layer; and b) said polymeric support layer comprising a blend of hydrocolloid and a polymeric material, said polymeric material consisting essentially of a polymeric material having a melting temperature of less than about 105° C.

19. The thin film device of claim 18 wherein said polymeric material is an ethylene vinyl acetate.

20. The thin film device of claim 17 wherein said ethylene vinyl acetate has a vinyl acetate content of from about 15% to about 28%.

21. The thin film device of claim 20 wherein said ethylene vinyl acetate has a vinyl content of about 18%.

22. The thin film device of claim 21 wherein said polymeric material and hydrocolloid have been extruded together.

23. The thin film device of claim 20 wherein said polymeric support layer is biaxially oriented.

24. The thin film device of claim 1 in the form of a skin-contacting baseplate for an ostomy appliance.

* * * * *

UNITED STATES PATENT AND TRADEMARK OFFICE
CERTIFICATE OF CORRECTION

PATENT NO. : 6,888,042 B1
DATED : May 3, 2005
INVENTOR(S) : Frank Freeman

It is certified that error appears in the above-identified patent and that said Letters Patent is hereby corrected as shown below:

Column 10,
Lines 15-21, should read as follows:
-- The thin film device of claim 17 wherein the wound dressing comprises:
a) said occlusive layer; and
b) said polymeric support layer comprising a blend of hydrocolloid and a polymeric material, said polymeric material consisting essentially of a polymeric material having a melting temperature of less than about 105°C. --
Line 38, please add claim 25 to read as follows:
-- A thin film device for medical applications comprising:
a) an occlusive layer having a perimeter and an edge portion about at least a portion of the perimeter of the occlusive layer and a body portion, said body portion being spaced apart from the user;
b) a non-continuous, hydrocolloid-containing polymeric support layer, being made of a material and constructed so as to permit rapid uptake of body fluids emanating from a wound, overlying the edge portion of the occlusive layer; and
c) a non-adhering layer attached to the polymeric support layer, said non-adhering layer having an adhesive thereon for attaching to the skin of the user. --

Signed and Sealed this

Nineteenth Day of July, 2005

JON W. DUDAS
*Director of the United States Patent and Trademark Office*